United States Patent
Gragoudas et al.

(10) Patent No.: US 7,803,375 B2
(45) Date of Patent: Sep. 28, 2010

(54) METHODS AND COMPOSITIONS FOR TREATING CONDITIONS OF THE EYE

(75) Inventors: Evangelos S. Gragoudas, Lexington, MA (US); Vassiliki Poulaki, Roslindale, MA (US); Joan W. Miller, Winchester, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 824 days.

(21) Appl. No.: 11/359,887

(22) Filed: Feb. 22, 2006

(65) Prior Publication Data

US 2006/0204504 A1 Sep. 14, 2006

Related U.S. Application Data

(60) Provisional application No. 60/655,723, filed on Feb. 23, 2005.

(51) Int. Cl.
- A61K 39/395 (2006.01)
- A61K 38/16 (2006.01)
- A61K 31/66 (2006.01)
- A61K 33/00 (2006.01)
- A61K 47/22 (2006.01)

(52) U.S. Cl. .............. 424/143.1; 424/130.1; 424/138.1; 424/155.1; 514/12; 514/185; 514/410; 540/145; 8/662

(58) Field of Classification Search .................. None
See application file for complete search history.

(56) References Cited

U.S. PATENT DOCUMENTS

| | | | |
|---|---|---|---|
| 5,091,513 A | 2/1992 | Huston et al. | |
| 5,132,405 A | 7/1992 | Huston et al. | |
| 5,258,498 A | 11/1993 | Huston et al. | |
| 5,482,858 A | 1/1996 | Huston et al. | |
| 5,756,541 A | 5/1998 | Strong et al. | |
| 5,798,349 A | 8/1998 | Levy et al. | |
| 5,840,719 A | 11/1998 | Rubin et al. | |
| 5,910,510 A | 6/1999 | Strong et al. | |
| 6,180,402 B1 | 1/2001 | Granville et al. | |
| 6,225,303 B1 | 5/2001 | Miller et al. | |
| 6,397,849 B1 | 6/2002 | Bowman et al. | |
| 6,433,147 B1 | 8/2002 | Ni et al. | |
| 6,455,040 B1 | 9/2002 | Wei et al. | |
| 6,506,569 B1 | 1/2003 | Ni et al. | |
| 6,623,941 B1 | 9/2003 | Ruben et al. | |
| 2002/0040015 A1* | 4/2002 | Miller et al. | |
| 2003/0008857 A1 | 1/2003 | Hunt et al. | |
| 2003/0083649 A1* | 5/2003 | Margaron et al. | |
| 2003/0104618 A1 | 6/2003 | Hughes | |
| 2004/0097425 A1 | 5/2004 | Shima et al. | |
| 2005/0129684 A1 | 6/2005 | Zacks et al. | |
| 2006/0204504 A1 | 9/2006 | Gragoudas et al. | |
| 2007/0032427 A1 | 2/2007 | Grosskreutz | |
| 2007/0287756 A1 | 12/2007 | Nakazawa | |

FOREIGN PATENT DOCUMENTS

| | | |
|---|---|---|
| WO | WO-00/51638 | 9/2000 |
| WO | WO00/61150 | 10/2000 |
| WO | WO-01/09327 | 2/2001 |
| WO | WO-03/061519 | 7/2003 |
| WO | WO-2005/105133 | 11/2005 |
| WO | WO-2006/091666 | 8/2006 |
| WO | WO-2007/019427 | 2/2007 |
| WO | WO-2008/063639 | 5/2008 |

OTHER PUBLICATIONS

Drolet et al. Pharmacokinetics and safety of an anti-vascular endothelial growth factor aptamer (NX1838) following injection into the vitreous humor of rhesus monkey, Pharm. Res. 17(12):1503-1510, 2000.*
Kaplan et al. Fas ligand (cd95 ligand) controls angiogenesis beneath the retina, Nat. Med. 5(3):292-297, Mar. 1999.*
Zacks et al., Fas-mediated apoptosis and its relation to intrinsic patheay activation in an expreimental model of retinal detachment, Invest. Ophth. Vis. Sci. 45:4563-4569, Dec. 2004.*
Mitsiades et al. Matric metalloproteinase-7-meidated cleavage of Fas ligand protects tumor cells from chemotherapeutic drug toxicity, Cancer Res. 61:577-581, Jan. 15, 2001.*
Joussen et al., Suppression of Fas-FasL-induced endothelial cell apoptosis prevetns diabetic blood-retinal barrier breakdown in a model of strptozotocin-induced diabetes, FASEB J. 17 :76-78, Jan. 2003.*
Chen et al., Photodynamic therapy with hypericin induces vascular damage and apoptosis in the RIF-1 mouse tumor model, Int. J. Cancer, 98:284-290, 2002.*
Il et al., Role of matrix metalloproteinase-7 (matrilysin) in human cancer invasion, apoptosis, growth, and angiogenesis, Exp. Biol. Med. 231:20-27, 2006.*
Hasegawa et al., Fas-disabling small exocyclic peptide mimetics limit apoptosis by an unexpected mechanism, Proc. Natl. Acad. Sci. USA, 101(17):6599-6604, Apr. 27, 2004.*
German et al., Docosahexaenoic acid prevents apoptosis of retina photoreceptors by activating the ERK/MAPK pathway, J. Neurochem. 98:1507-1520, 2006.*

(Continued)

Primary Examiner—Elizabeth C. Kemmerer
Assistant Examiner—Claire Kaufman
(74) Attorney, Agent, or Firm—Goodwin Procter LLP

(57) ABSTRACT

Provided are methods and compositions for treating ocular conditions characterized by the presence of unwanted choroidal neovasculature, for example, neovascular age-related macular degeneration. The selectivity and sensitivity of, for example, a photodynamic therapy (PDT)-based approach can be enhanced by combining the PDT with an anti-FasL factor, for example, an anti-FasL neutralizing antibody.

15 Claims, 10 Drawing Sheets

OTHER PUBLICATIONS

Adamis et al. (1996) "Inhibition of vascular endothelial growth factor prevents retinal ischemia-associated iris neovascularization in a non-human primate" Arch. Ophthalmol. 114:66-71.

Aiello et al. (1994) "Vascular endothelial growth factor in ocular fluid of patients with diabetic retinopathy and other retinal disorders" Surv. Ophthalmol. 331(22):1480-7.

Aoudjit et al. (2001) Matrix attachment regulates Fas-induced apopotosis in endothelial cells: a role for c-flip and implications for anoikis J. Cell Biol. 152(3):633-43, abstract.

Arap et al. (1998) "Cancer treatment by targeted drug delivery to tumor vasculature in a mouse model" Science 279:377-380.

Bressler et al. (1988) "Age-related macular degeneration" Surv. Ophthalmol. 32:375-413.

Bressler et al. (2001) "Photodynamic therapy of subfoveal choroidal neovascularization in age-related macular degeneration with verteporfin: two-year results of 2 randomized clinical trials-tap report 2" Arch Opthalmol 119(2): 198-207.

Brooks et al. (1994) "Requirement of vascular integrin $\alpha_v\beta_3$ for angiogenesis" Science 264: 569-571.

Bula et al. (2004) "Pigment epithelium-derived factor, Angiopoietin-1 and VEGF expression in human choroidal neovascular membranes treated with photodynamic therapy" Invest. Ophthalmol. Vis. Sci. 45: E-Abstract 1787 (first available on Feb. 23, 2004, at ARVO website, www.arvo.org).

Cook et al. (1995) "Apoptotic photoreceptor degeneration in experimental retinal detachment," Invest Ophthalmol Vis Sci. 36: 990-996.

Corjay et al. (1997) "$\alpha_v\beta_3$, $\alpha_v\beta_5$ and osteopontin immunostaining in experimental choroidal neovascularization in the monkey" Invest. Othamol. Vis. Sci. 38, S965, abstract.

Delgado et al. (2001) "Vasoactive intestinal peptide and pituitary adenylate cyclase-activating polypeptide inhibit expression of Fas ligand in activated T lymphocytes by regulating c-Myc, NF-kappa B, NF-AT, and early growth factors 2/3" J. Immunol. 166(2):1028-40.

Dockrell (2003) "The multiple roles of Fas ligand in the pathogenesis of infectious diseases" Clin Microbiol Infect. 9(8): 766-79.

Dunaief et al. (2002) "The role of apoptosis in age-related macular degeneration" Arch. Ophthalmol. 120: 1435-42.

Eberl et al. (2000) "Endothelin receptor blockade potentiates FasL-induced apoptosis in colon carcinoma cells via the protein kinase C-pathway" J Cardiovasc Pharmacol. 36(5 Suppl 1):S354-6, abstract.

Eberl et al. (2000) "Endothelin receptor blockade potentiates FasL-induced apoptosis in rat colon carcinoma cells" Int. J. Cancer 86: 182-7, abstract.

Ellerby et al. (1999) "Anti-cancer activity of targeted pro-apoptotic peptides" Nature Medicine 5: 1032-1038.

Farkas et al. (2001) "Apoptosis, neuroprotection, and retinal ganglion cell death: an overview" Int. Opthalmol. Clinic. 41(1): 111-130.

Folkman (1995) "Angiogenesis in cancer, vascular, rheumatoid and other disease" Nature Medicine 1:27-31.

Freeman et al. (2000) "The effects of FK506 on retinal ganglion cells after optic nerve crush," Invest Ophthalmol Vis Sci. 41: 1111-15.

Freund et al. (1993) "Age-related macular degeneration and choroidal neovascularization" Am. J. Ophthalmol. 115: 786-91.

Friedlander et al. (1995) "Definition of two angiogenic pathways by distinct $\alpha_v$ integrins" Science 270: 1500-1502.

Friedlander et al. (1996) "Involvement of integrins $\alpha_v\beta_3$ and $\alpha_v\beta_5$ in ocular neovascular diseases" Proc. Natl. Acad. Sci. USA 93:9764-9769.

Gregory et al. (1995) "Cell loss in retinal dystrophies by apoptosis—death by informed consent" Brit. J. Ophthalmol. 79: 186-190.

Granville et al. (2001) "Fas ligand and Trail augment the effect of photodynamic therapy on the induction of apoptosis in JURKAT cells" Int Immunopharmacol. 1(9-10):1831-40, abstract.

Granville et al. (1999) "Bcl-2 overexpression blocks caspase activation and downstream apoptotic events instigated by photodynamic therapy" Br J Cancer 79(1): 95-100.

Grosskreutz et al. (2005) "FK506 blocks activation of the intrinsic caspase cascade after optic nerve crush," Exp Eye Res. 80(5):681-86.

Guyer et al. (1986) "Subfoveal choroidal neovascular membranes in age-related macular degeneration. Visual prognosis in eyes with relatively good initial visual acuity" Arch. Ophthalmol. 104:702-705.

Han et al. (2004) Effects of the combined use of benazepril and valsartan on apoptosis in the kidney of rats with adriamycin-induced nephritic glomerulosclerosis, Huazhong Univ. Sci. Technolog. Med. Sci. 24: 254-8, abstract.

Hasegawa et al. (2004) "Fas-disabling small exocyclic peptide mimetics limited aptopsis by an unexpected mechanism" Proc. Natl. Acad. Sci. U.S.A. 101(17):6599-604, abstract.

Hisatomi et al. (2002) "Critical Role of photoreceptor apoptosis in functional damage after retinal detachment," Curr. Eye Res. 24(3): 161-172.

Hisatomi et al. (2001) "Relocalization of apoptosis-inducing factor in photoreceptor apoptosis induced by retinal detachment in vivo," Am. J. of Pathol. 158(4):1271-78.

Hyman et al. (1983) "Senile macular degeneration: a case-control study" Am. J. Epidemiol. 118(2):213-27.

International Search Report for Application No. PCT/US2006/006272, dated Mar. 15, 2007 (3 pages).

Ishida et al. (2003) "Leukocytes mediate retinal vascular remodeling during development and vasoobliteration in disease" Nat Med. 9(6):781-88.

Ivanov et al. (1997) "Regulation of Fas-dependent activation-induced T cell apoptosis by cAMP signaling: a potential role for transcription factor NF-kappaB" Oncogene 14: 2455-64, abstract.

Kikuchi et al. (1998) "Protective effects of FK506 against glutamate-induced neurotoxicity in retinal cell culture," Invest Ophthalmol Vis Sci. 39(7):1227-32.

Klein & Klein (1982) "Cataracts and macular degeneration in older Americans" Arch. Ophthalmol. 100:571-573.

LaVail et al. (1998) "Protection of mouse photoreceptors by survival factors in retinal degenerations" Invest. Ophthalmol. Vis. Sci. 39(3): 592-602.

Le et al. (2002) "PAC1 and PACAP expression, signaling, and effect on the growth of HCT8, human colonic tumor cells" 15;109(1-3):115-25, abstract.

Leibowitz et al. (1980) "The Framingham Eye Study monograph: An ophthalmological and epidemiological study of cataract, glaucoma, diabetic retinopathy, macular degeneration, and visual acuity in a general population of 2631 adults 1973-1975" Surv. Ophthalmol. 24:335-610, (Title page, Abstract, Table of Contents, and Preface provided).

Lewis et al. (1999) "Effects of the neurotrophin brain-derived neurotrophic factor in an experimental model of retinal detachment" Invest. Ophthalmol. Vis. Sci. 40(7): 1530-44.

Macular Photocoagulation Study Group (1991) "Laser photocoagulation of subfoveal neovascular lesions in age-related macular degeneration: Results of a randomized clinical trial" Arch. Ophthalmol. 109:1220-31.

Makrigiannakis et al. (2004) "Endometrial and placental CRH as regulators of human embryo implantation" J. Reprod. Immunol. 62:53-9, abstract.

Makrigiannakis et al. (2004) "Participation of maternal and fetal CRH in early phases of human implantation: the role of antalarmin" Current Drug Targets Immune Endoc. Matabol. Disord. 4(1):75-8, abstract.

Martin-Villalba et al. (2001) "Therapeutic neutralization of CD95-ligand and TNF attenuates brain damage in stroke" Cell Death Differ. 8(7):679-86.

Miller et al. (1999) "Photodynamic therapy with verteporfin for choroidal neovascularisation caused by age-related macular degeneration: Results of a single treatment in a phase 1 and 2 study" Arch. Ophthalmol. 117:1161-73.

Moser et al. (1999) "Angiostatin binds ATP synthase on the surface of human endothelial cells" Proc. Natl. Acad. Sci. USA 96:2811-2816.

Murohisa et al. (2002) "Involvement of platelet-activating factor in hepatic apoptosis and necrosis in chronic ethanol-fed rats given endotoxin" Liver 22:394-403, abstract.

Nagata et al. (1994) "Fas and Fas ligand: a death factor and its receptor" Adv Immunol. 57:129-44.

O'Connell (2001) "Role of Fas-FasL in inflammatory diseases" Expert Reviews in Molecular Medicine Cambridge U. Press, pp. 1-18.

Ortiz et al. (1999) "The Fas ligand/ Fas system in renal injury" Nephrol Dial Transplant 14:1831-34:1831.

Okuda et al. (2000) "Intrathecal administration of neutralizing antibody against Fas ligand suppresses the progression of experimental autoimmune encephalomyelitis" Biochem. Biphys. Res. Commun. 275(1):164-8.

Pasqualini et al. (1996) "Organ targeting in vivo using phage display peptide libraries" Nature 380:364-366.

Poulaki et al. (2001) "Fas/Fas ligand-associated apoptosis in experimental autoimmune uveoretinitis in rodents: role of proinflammatory corticotropin—releasing hormone" Exp Eye Res. 72(6):623-629.

Poulaki et al. (2005) "Anti-FasL neutralizing antibody increases the efficacy of PDT and reduces the apoptotic damage in a rat laser model" Invest Ophthalmol Vis Sci. 46: E-Abstract 185 (first available on Feb. 22, 2005, at ARVO website, www.arvo.org).

Poulaki et al. (2004) "Insulin-like growth factor-I plays a pathogenetic role in diabetic retinopathy" Am J Pathol 165(2): 457-469.

Poulaki et al. (2002) "Acute intensive insulin therapy exacerbates diabetic blood-retinal barrier breakdown via hypoxia-inducible factor-1α and VEGF" J clin Invest 109(6): 805-815.

Quirk et al. (2004) "Progesterone receptor and the cell cycle modulate apoptosis in granulosa cells" Endocrinology 145:5033-43, abstract.

Rieux-Laucat et al. (2003) "Cell-death signaling and human disease" Curr. Opin. Immunol. 15(3):325-31.

Schulze-Osthoff et al. (1998) "Apoptosis signaling by death receptors" Eur J Biochem. 254(3):439-459.

Tolentino et al. (1996) "Vascular endothelial growth factor is sufficient to produce iris neovascularization and neovascular glaucoma in a nonhuman primate" Arch. Ophthalmol. 114:964-970.

Tolentino et al. (1996) "Intravitreous injections of vascular endothelial growth factor produce retinal ischemia and microangiopathy in an adult primate" Ophthalmology 103:1820-1828.

Wigginton et al. (2001) "IFN-γ and Fas/FasL are required for the antitumor and antiangiogenic effects of IL-12/pulse IL-2 therapy" J. Clin. Invest. 108:51-62.

Wortinger et al. (2003) "Fas ligand-induced murine pulmonary inflammation is reduced by a stale decoy receptor 3 analogue" Immunology 110(2):225-33.

Zacks et al. (2002) "Verteporfin photodynamic therapy in the rat model of choroidal neovascularization: angiographic and histologic characterization" Invest Ophthalmol Vis Sci. 43(7):2383-2391.

Zacks et al. (2007) "Role of the FAS-signaling pathway in photoreceptor neuroprotection" Arch. Ophthalmol. 125(10):1389-1395.

Nyhus et al. (2001) "Direct in vivo transfection of antisense Fas-ligand reduces tumor growth and invasion," Gene Therapy, 8, pp. 209-214.

Song et al. (2003) "RNA interference targeting Fas protects mice from fulminant hepatitis," Nature Medicine 9, pp. 347-351 (Abstract).

Wang et al. (2003) "Fas siRNA reduces apoptotic cell death of allogenic-transplanted hepatocytes in mouse spleen," Transplant Proc. 35(4) pp. 1594-1595 (Abstract).

Yin (2000) "Signal transduction mediated by Bid, a pro-death Bcl-2 family proteins, connects the death receptor and mitochondria apoptosis pathways," Cell Research, 10, pp. 161-167.

Yoshizawa, K. et al. (2000) "Capsase-3 Inhibitor, Rescues N-Methyl-N-nitrosourea-induced Retinal Degeneration in Sprague-Dawley Rats," Exp. Eye Res. vol. 71, pp. 629-635.

Yu et al. (2001) "Pharmacokinetics and Pharmacodynamics of an Antisense Phosphorothioate Oligonucleotide Targeting Fas mRNA in Mice," J. of Pharmacology and Experimental Therapeutics, vol. 296, No. 2, pp. 388-395.

Zhang et al. (2000) "Reduction of liver Fas expression by an antisense oligonucleotide protects mice from fulminant hepatitis," Nat Biotechnol. 18(8) pp. 862-867 (Abstract).

Zou et al. (2007) "Lack of Fas antagonism by Met in human fatty liver disease," Nature, vol. 13, No. 9, 1078-1085.

\* cited by examiner

|  | Open | Closed | Total |
|---|---|---|---|
| Control Ab | 4 | 9 | 13 |
| Anti FasL Ab | 0 | 15 | 15 |

Figure 5

|  | Grade 0+I | Grade IIA+IIB | Total |
|---|---|---|---|
| Control Ab | 1 | 37 | 38 |
| Anti FasL Ab | 8 | 36 | 44 |

Figure 6

METHODS AND COMPOSITIONS FOR TREATING CONDITIONS OF THE EYE

CROSS-REFERENCE TO RELATED APPLICATION

The present application claims the benefit of and priority to U.S. Patent Application Ser. No. 60/655,723, filed Feb. 23, 2005, the entire disclosure of which is incorporated by reference herein for all purposes.

FIELD OF THE INVENTION

The invention relates generally to methods and compositions for treating ocular conditions and, more specifically, the invention relates to photodynamic therapy-based methods and compositions for treating ocular conditions characterized by unwanted choroidal neovasculature.

BACKGROUND

Choroidal neovascularization can lead to hemorrhage and fibrosis, with resulting visual loss in a number of conditions of the eye, including, for example, age-related macular degeneration, ocular histoplasmosis syndrome, pathologic myopia, angioid streaks, idiopathic disorders, choroiditis, choroidal rupture, overlying choroid nevi, and certain inflammatory diseases. One of the disorders, namely, age-related macular degeneration (AMD), is the leading cause of severe vision loss in people aged 65 and above (Bressler et al. (1988) Surv. Ophthalmol. 32, 375-413, Guyer et al. (1986) Arch. Ophthalmol. 104, 702-705, Hyman et al. (1983) Am. J. Epidemiol. 188, 816-824, Klein & Klein (1982) Arch. Ophthalmol. 100, 571-573, Leibowitz et al. (1980) Surv. Ophthalmol. 24, 335-610). Although clinicopathologic descriptions have been made, little is understood about the etiology and pathogenesis of the disease.

Dry AMD is the more common form of the disease, characterized by drusen, pigmentary and atrophic changes in the macula, with slowly progressive loss of central vision. Wet or neovascular AMD is characterized by subretinal hemorrhage, fibrosis and fluid secondary to the formation of choroidal neovasculature (CNV), and more rapid and pronounced loss of vision. While less common than dry AMD, neovascular AMD accounts for 80% of the severe vision loss due to AMD. Approximately 200,000 cases of neovascular AMD are diagnosed yearly in the United States alone.

Currently, treatment of the dry form of age-related macular degeneration includes administration of antioxidant vitamins and/or zinc. Treatment of the wet form of age-related macular degeneration, however, has proved to be more difficult. Currently, two separate methods have been approved in the United States of America for treating the wet form of age-related macular degeneration. These include laser photocoagulation and photodynamic therapy (PDT) using a benzoporphyrin derivative photosensitizer. During laser photocoagulation, thermal laser light is used to heat and photocoagulate the neovasculature of the choroid. A problem associated with this approach is that the laser light must pass through the photoreceptor cells of the retina in order to photocoagulate the blood vessels in the underlying choroid. As a result, this treatment destroys the photoreceptor cells of the retina creating blind spots with associated vision loss. During photodynamic therapy, a benzoporphyrin derivative photosensitizer is administered to the individual to be treated. Once the photosensitizer accumulates in the choroidal neovasculature, non-thermal light from a laser is applied to the region to be treated, which activates the photosensitizer in that region. The activated photosensitizer generates free radicals that damage the vasculature in the vicinity of the photosensitizer (see, U.S. Pat. Nos. 5,798,349 and 6,225,303). This approach is more selective than laser photocoagulation and is less likely to result in blind spots. Under certain circumstances, this treatment has been found to restore vision in patients afflicted with the disorder (see, U.S. Pat. Nos. 5,756,541 and 5,910,510).

During clinical studies, however, it has been found that recurrence of leakage appears in at least a portion of the CNV by one to three months post-treatment. Increasing photosensitizer or light doses do not appear to prevent this recurrence, and can even lead to undesired non-selective damage to retinal vessels (Miller et al. (1999) Archives of Ophthalmology 117: 1161-1173). Another avenue of investigation is to repeat the PDT procedure over prolonged periods of time. The necessity for repeated PDT treatments can nevertheless be expected to lead to cumulative damage to the retinal pigment epithelium (RPE) and choriocapillaris, which may lead to progressive treatment-related vision loss. In addition, PDT can cause transient visual disturbances, injection-site adverse effects, transient photosensitivity reactions, infusion-related back pain, and vision loss.

Therefore, there is still a need for improved methods for treating AMD characterized by unwanted choroidal neovasculature that increase the efficacy and selectivity of treatment, and which reduce or delay a recurrence of the disorder.

SUMMARY OF THE INVENTION

The present invention is directed to methods and compositions for treating ocular conditions associated with unwanted choroidal neovasculature. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases. The invention, for example, provides a more effective PDT-based method for treating unwanted CNV that has one or more of the following advantages: increased efficacy of treatment; increased selectivity for CNV; and reduced or delayed recurrence of the condition following PDT.

In one aspect, the invention provides a method of treating unwanted CNV in a mammal, wherein the CNV comprises endothelial cells, for example, capillary endothelial cells. The method comprises the steps of: (a) administering to the mammal, for example, a primate, preferably, a human, an anti-FasL factor in an amount sufficient to permit an effective amount to localize in the CNV; (b) administering to the mammal an amount of a photosensitizer (PDT dye) sufficient to permit an effective amount to localize in the CNV; and (c) irradiating the CNV with laser light such that the light is absorbed by the photosensitizer so as to occlude the CNV. During practice of this method, the anti-FasL factor can enhance the activity of PDT. For example, the anti-FasL factor and the PDT may act synergistically.

A variety of anti-FasL factors may be used in the invention. Useful anti-FasL factors, include, for example, anti-FasL neutralizing antibody (available, for example, from Pharmingen, San Diego, Calif.); peptides and nucleic acids (for example, anti-FasL aptamers) that bind FasL to prevent or reduce its binding to its cognate receptor; certain antibodies and antigen binding fragments thereof and peptides that bind preferentially to the Fas receptor; antisense nucleotides and double stranded RNA for RNAi that ultimately reduce or eliminate the production of either FasL or the Fas receptor;

soluble Fas; soluble FasL; decoy receptor-3 (DcR3) analogues; matrix metalloproteinases (MMPs); vasoactive intestinal peptide (VIP); pituitary adenylate cyclase-activating polypeptide (PACAP); forskolin; combined use of benazepril and valsartan; nonpeptidic corticotropin-releasing hormone receptor type 1 (CRH-R1)-specific antagonists; mimosine; peptides that produce a defective Fas-FasL complex; platelet-activating factor (PAF); and endothelin-1(ET-1). These anti-FasL factors can act as direct or indirect antagonists of FasL activity.

The term "antibody," as used herein, includes, for example, a monoclonal antibody or an antigen binding fragment thereof (for example, an Fv, Fab, Fab' or an (Fab')$_2$ molecule), a polyclonal antibody or an antigen binding fragment thereof, or a biosynthetic antibody binding site, for example, an sFv (U.S. Pat. Nos. 5,091,513; 5,132,405; 5,258,498; and 5,482,858) that binds specifically to a target ligand. As used herein, the terms binds "specifically" or "preferentially" are understood to mean that the targeting molecule, for example, the antibody, binds to the complementary or target ligand with a binding affinity of at least $10^5$ M$^{-1}$, and more preferably $10^7$ M$^{-1}$.

The anti-FasL factor may, under certain circumstances, be co-administered simultaneously with the photosensitizer. Alternatively, the anti-FasL factor may be administered before or after the photosensitizer. In a preferred embodiment, however, the anti-FasL factor is administered to the mammal prior to administration of the photosensitizer.

In another aspect, the invention provides an improved method of treating unwanted choroidal neovasculature in a mammal. The improvement includes administering to the mammal an effective amount of an anti-FasL factor so as to relieve side effects associated with a method for treating unwanted choroidal neovasculature. The anti-FasL factor can include an anti-FasL antibody, and the side effects can include photoreceptor cell death. In certain instances, the anti-FasL factor reduces apoptotic cell death of photoreceptor cells during the method of treating unwanted choroidal neovasculature. The method of treating unwanted choroidal neovasculature can include photodynamic therapy using a benzoporphyrin derivative photosensitizer; can include administering an effective amount of an anti-VEGF aptamer, an effective amount of an anti-VEGF antibody, and/or an effective amount of an anti-VEGF siRNA; and/or can include ameliorating the symptoms of age-related macular degeneration.

In all the methods disclosed herein, it is contemplated that any photosensitizer useful in PDT may be useful in the practice of the invention. Useful photosensitizers include, for example, amino acid derivatives, azo dyes, xanthene derivatives, chlorins, tetrapyrrole derivatives, phthalocyanines, and assorted other photosensitizers. Preferred photosensitizers, include, for example, lutetium texaphyrin, benzoporphyrin and derivatives thereof, and hematoporphyrin and derivatives thereof.

BRIEF DESCRIPTION OF THE DRAWINGS

The foregoing and other objects, features, and advantages of the present invention, as well as the invention itself, may be more fully understood from the following description of preferred embodiments, when read together with the accompanying drawings, in which:

FIG. 5 provides evidence that anti-FasL treatment reduces angiographic leakage after PDT;

FIG. 6 provides evidence that anti-FasL treatment reduces angiographic leakage in laser-induced CNV;

DETAILED DESCRIPTION OF THE INVENTION

Figure 1:
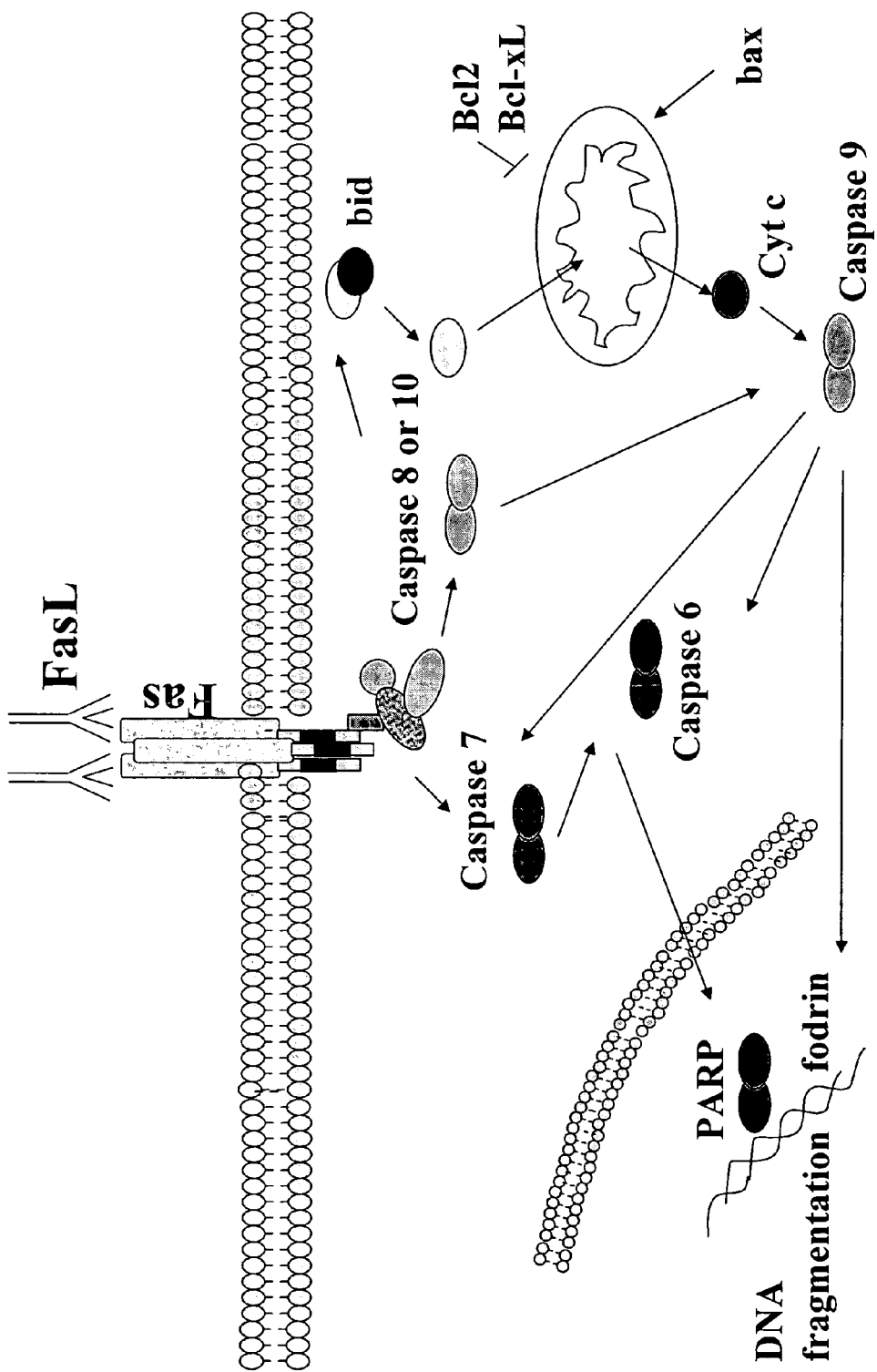
FIG. 1 depicts a schematic drawing of the FasL apoptotic pathway.

The invention relates to an improved method for treating ocular conditions characterized as having unwanted CNV. Such conditions include, for example, neovascular AMD, ocular histoplasmosis syndrome, pathologic myopia, angioid streaks, idiopathic disorders, choroiditis, choroidal rupture, overlying choroid nevi, and certain inflammatory diseases. The invention provides one or more of the following advantages: increased efficacy of treatment; increased selectivity for CNV; and reduced or delayed recurrence of the condition following PDT.

The invention provides an improved method for treating ocular disorders, for example, AMD, characterized by unwanted choroidal neovasculature. The improved method comprises administering to the mammal an effective amount of an anti-FasL factor, for example, an anti-FasL antibody, for preserving photoreceptor viability, i.e., reducing collateral retinal damage during a treatment of unwanted choroidal neovasculature. For example, the anti-FasL factor may be combined with an anti-VEGF aptamer, for example the Macugen® aptamer (see the URL address eyetk.com/science/science_vegf.asp), for treatment of AMD (available from Eyetech Pharmaceuticals, Inc., NY, N.Y.). Alternatively, the anti-FasL factor may be combined with a VEGF specific RNAi for the treatment of AMD (see the URL address: alnylam.com/therapeutic-programs/programs. asp) (available from Alnylam Pharmaceuticals, Cambridge, Mass.). Similarly, the anti-FasL factor may be combined with an anti-VEGF antibody or antibody fragment for the treatment of AMD (see the URL address: gene.com/gene/products/information/oncology/avastin/index.jsp) (available from Genentech, Inc., San Francisco, Calif.).

In one aspect, the invention provides an improved PDT-based method for treating unwanted target CNV. The method involves administration of a photosensitizer to a mammal in need of such treatment in an amount sufficient to permit an effective amount (i.e., an amount sufficient to facilitate PDT) of the photosensitizer to localize in the target CNV. After administration of the photosensitizer, the CNV then is irradiated with laser light under conditions such that the light is absorbed by the photosensitizer. The photosensitizer, when activated by the light, generates singlet oxygen and free radicals, for example, reactive oxygen species, that result in damage to surrounding tissue. For example, PDT-induced damage of endothelial cells results in platelet adhesion and degranulation, leading to stasis and aggregation of blood cells and vascular occlusion.

An increase in efficacy and/or selectivity of the PDT, and/or reduction or delay of recurrence of the CNV, can be achieved by administering an anti-FasL factor to the mammal prior to, concurrent with, or after administration of the photosensitizer. It is contemplated that a variety of photosensitizers useful in PDT may be useful in the practice of the invention and include, for example, amino acid derivatives, azo dyes, xanthene derivatives, chlorins, tetrapyrrole derivatives, phthalocyanines, and assorted other photosensitizers.

Amino acid derivatives include, for example, 5-aminolevulinic acid (Berg et al. (1997) Photochem. Photobiol. 65: 403-409; El-Far et al. (1985) Cell. Biochem. Function 3, 115-119). Azo dyes, include, for example, Sudan I, Sudan II, Sudan III, Sudan IV, Sudan Black, Disperse Orange, Disperse Red, Oil Red O, Trypan Blue, Congo Red, β-carotene (Mosky et al. (1984) Exp. Res. 155, 389-396). Xanthene derivatives, include, for example, rose bengal.

Chlorins include, for example, lysyl chlorin p6 (Berg et al. (1997) supra) and etiobenzochlorin (Berg et al. (1997) supra), 5, 10, 15, 20-tetra (m-hydroxyphenyl) chlorin (M-THPC), N-aspartyl chlorin e6 (Dougherty et al. (1998) J. Natl. Cancer Inst. 90: 889-905), and bacteriochlorin (Korbelik et al. (1992) J. Photochem. Photobiol. 12: 107-119).

Tetrapyrrole derivatives include, for example, lutetium texaphrin (Lu-Tex, PCI-0123) (Dougherty et al. (1998) supra, Young et al. (1996) Photochem. Photobiol. 63: 892-897), benzoporphyrin derivative (BPD) (U.S. Pat. Nos. 5,171,749, 5,214,036, 5,283,255, and 5,798,349, Jori et al. (1990) Lasers Med. Sci. 5, 115-120), benzoporphyrin derivative mono acid (BPD-MA) (U.S. Pat. Nos. 5,171,749, 5,214,036, 5,283,255, and 5,798,349, Berg et al. (1997) supra, Dougherty et al. (1998) supra), hematoporphyrin (Hp) (Jori et al. (1990) supra), hematoporphyrin derivatives (HpD) (Berg et al. (1997) supra, West et al. (1990) In. J. Radiat. Biol. 58: 145-156), porfimer sodium or Photofrin (PHP) (Berg et al. (1997) supra), Photofrin II (PII) (He et al. (1994) Photochem. Photobiol. 59: 468-473), protoporphyrin IX (PpIX) (Dougherty et al. (1998) supra, He et al. (1994) supra), meso-tetra (4-carboxyphenyl) porphine (TCPP) (Musser et al. (1982) Res. Commun. Chem. Pathol. Pharmacol. 2, 251-259), meso-tetra (4-sulfonatophenyl) porphine (TSPP) (Musser et al. (1982) supra), uroporphyrin I (UROP-I) (El-Far et al. (1985) Cell. Biochem. Function 3, 115-119), uroporphyrin III (UROP-III) (El-Far et al. (1985) supra), tin ethyl etiopurpurin (SnET2), (Dougherty et al. (1998) supra 90: 889-905) and 13, 17-bis [1-carboxypropionyl] carbamoylethyl-8-etheny-2-hydroxy-3-hydroxyiminoethyliden e-2,7,12,18-tetranethyl 6 porphyrin sodium (ATX-S10(Na)) Mori et al. (2000) JPN. J. CANCER RES. 91:753-759, Obana et al. (2000) Arch. Ophthalmol. 118:650-658, Obana et al. (1999) Lasers Surg. Med. 24:209-222).

Phthalocyanines include, for example, chloroaluminum phthalocyanine (AlPcCl) (Rerko et al. (1992) Photochem. Photobiol. 55, 75-80), aluminum phthalocyanine with 2-4 sulfonate groups (AlPcS2-4) (Berg et al. (1997) supra, Glassberg et al. (1991) Lasers Surg. Med. 11, 432-439), chloroaluminum sulfonated phthalocyanine (CASPc) (Roberts et al. (1991) J. Natl. Cancer Inst. 83, 18-32), phthalocyanine (PC) (Jori et al. (1990) supra), silicon phthalocyanine (Pc4) (He et al. (1998) Photochem. Photobiol. 67: 720-728, Jori et al. (1990) supra), magnesium phthalocyanine (Mg2+-PC) (Jori et al. (1990) supra), and zinc phthalocyanine (ZnPC) (Berg et al. (1997) supra). Other photosensitizers include, for example, thionin, toluidine blue, neutral red and azure c.

However, useful photosensitizers, include, for example, Lutetium Texaphyrin (Lu-Tex), a new generation photosensitizer having favorable clinical properties including absorption at about 730 nm permitting deep tissue penetration and rapid clearance. Lu-Tex is available from Alcon Laboratories, Fort Worth, Tex. Other useful photosensitizers include benzoporhyrin and benzoporphyrin derivatives, for example, BPD-MA and BPD-DA, available from QLT Inc., Vancouver, Canada.

The photosensitizer preferably is formulated into a delivery system that delivers high concentrations of the photosensitizer to the CNV. Such formulations may include, for example, the combination of a photosensitizer with a carrier that delivers higher concentrations of the photosensitizer to CNV and/or coupling the photosensitizer to a specific binding ligand that binds preferentially to a specific cell surface component of the CNV.

In one embodiment, the photosensitizer can be combined with a lipid based carrier. For example, liposomal formulations have been found to be particularly effective at delivering the photosensitizer, green porphyrin, and more particularly BPD-MA to the low-density lipoprotein component of plasma, which in turn acts as a carrier to deliver the photosensitizer more effectively to the CNV. Increased numbers of LDL receptors have been shown to be associated with CNV, and by increasing the partitioning of the photosensitizer into the lipoprotein phase of the blood, it may be delivered more efficiently to the CNV. Certain photosensitizers, for example, green porphyrins, and in particular BPD-MA, interact strongly with lipoproteins. LDL itself can be used as a carrier, but LDL is more expensive and less practical than a liposomal formulation. LDL, or preferably liposomes, are thus preferred carriers for the green porphyrins since green porphyrins strongly interact with lipoproteins and are easily packaged in liposomes. Compositions of green porphyrins formulated as lipocomplexes, including liposomes, are described, for example, in U.S. Pat. Nos. 5,214,036, 5,707,608 and 5,798,349. Liposomal formulations of green porphyrin can be obtained from QLT Inc., Vancouver, Canada. It is contemplated that certain other photosensitizers may likewise be formulated with lipid carriers, for example, liposomes or LDL, to deliver the photosensitizer to CNV.

Furthermore, the photosensitizer can be coupled or conjugated to a targeting molecule that targets the photosensitizer to CNV. For example, the photosensitizer may be coupled or conjugated to a specific binding ligand that binds preferentially to a cell surface component of the CNV, for example, neovascular endothelial homing motif. It appears that a variety of cell surface ligands are expressed at higher levels in new blood vessels relative to other cells or tissues.

Endothelial cells in new blood vessels express several proteins that are absent or barely detectable in established blood vessels (Folkman (1995) Nature Medicine 1:27-31), and include integrins (Brooks et al. (1994) Science 264: 569-571; Friedlander et al. (1995) Science 270: 1500-1502) and receptors for certain angiogenic factors like vascular endothelial growth factor (VEGF). In vivo selection of phage peptide libraries have also identified peptides expressed by the vasculature that are organ-specific, implying that many tissues have vascular "addresses" (Pasqualini et al. (1996) Nature 380: 364-366). It is contemplated that a suitable targeting moiety can direct a photosensitizer to the CNV endothelium thereby increasing the efficacy and lowering the toxicity of PDT.

Several targeting molecules may be used to target photosensitizers to the neovascular endothelium. For example, α-v integrins, in particular α-v β3 and α-v β5, appear to be expressed in ocular neovascular tissue, in both clinical specimens and experimental models (Corjay et al. (1997) Invest. Ophthalmol. Vis. Sci. 38, S965; Friedlander et al. (1995)

supra). Accordingly, molecules that preferentially bind α-v integrins can be used to target the photosensitizer to CNV. For example, cyclic peptide antagonists of these integrins have been used to inhibit neovascularization in experimental models (Friedlander et al. (1996) Proc. Natl. Acad. Sci. USA 93:9764-9769). A peptide motif having an amino acid sequence, in an N-to C-terminal direction, ACDCRGDCFC (SEQ ID NO: 1)—also know as RGD-4C—has been identified that selectively binds to human α-v integrins and accumulates in tumor neovasculature more effectively than other angiogenesis targeting peptides (Arap et al. (1998) Nature 279:377-380; Ellerby et al. (1999) Nature Medicine 5: 1032-1038). Angiostatin may also be used as a targeting molecule for the photosensitizer. Studies have shown, for example, that angiostatin binds specifically to ATP synthase disposed on the surface of human endothelial cells (Moser et al. (1999) Proc. Natl. Acad. Sci. USA 96:2811-2816).

Clinical and experimental evidence strongly supports a role for vascular endothelial growth factor (VEGF) in ocular neovascularization, particularly ischemia-associated neovascularization (Adamis et aL (1996) Arch. Ophthalmol. 114: 66-71; Tolentino et al. (1996) Arch. Ophthalmol. 114:964-970; Tolentino et al. (1996) Ophthalmology 103:1820-1828). Potential targeting molecules include antibodies that bind specifically to either VEGF or the VEGF receptor (VEGF-2R). Antibodies to the VEGF receptor (VEGFR-2 also known as KDR) may also bind preferentially to neovascular endothelium.

The targeting molecule may be synthesized using methodologies known and used in the art. For example, proteins and peptides may be synthesized using conventional synthetic peptide chemistries or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press. Once created, the targeting agent may be coupled or conjugated to the photosensitizer using standard coupling chemistries, using, for example, conventional cross linking reagents, for example, heterobifunctional cross linking reagents available, for example, from Pierce, Rockford, Ill.

Once formulated, the photosensitizer may be administered in any of a wide variety of ways, for example, orally, parenterally, or rectally. Parenteral administration, such as intravenous, intramuscular, or subcutaneous, is preferred. Intravenous injection is especially preferred. The dose of photosensitizer can vary widely depending on the tissue to be treated; the physical delivery system in which it is carried, such as in the form of liposomes; or whether it is coupled to a target-specific ligand, such as an antibody or an immunologically active fragment.

It should be noted that the various parameters used for effective, selective photodynamic therapy in the invention are interrelated. Therefore, the dose should also be adjusted with respect to other parameters, for example, fluence, irradiance, duration of the light used in PDT, and time interval between administration of the dose and the therapeutic irradiation. All of these parameters should be adjusted to produce significant damage to CNV without significant damage to the surrounding tissue.

Typically, the dose of photosensitizer used is within the range of from about 0.1 to about 20 mg/kg, preferably from about 0.15 to about 5.0 mg/kg, and even more preferably from about 0.25 to about 2.0 mg/kg. Furthermore, as the dosage of photosensitizer is reduced, for example, from about 2 to about 1 mg/kg in the case of green porphyrin or BPD-MA, the fluence required to close CNV may increase, for example, from about 50 to about 100 Joules/cm$^2$. Similar trends may be observed with the other photosensitizers discussed herein.

After the photosensitizer has been administered, the CNV is irradiated at a wavelength typically around the maximum absorbance of the photosensitizer, usually in the range from about 550 nm to about 750 nm. A wavelength in this range is especially preferred for enhanced penetration into bodily tissues. Preferred wavelengths used for certain photosensitizers include, for example, about 690 nm for benzoporphyrin derivative mono acid, about 630 nm for hematoporphyrin derivative, about 675 nm for chloro-aluminum sulfonated phthalocyanine, about 660 nm for tin ethyl etiopurpurin, about 730 nm for lutetium texaphyrin, about 670 nm for ATX-S10(NA), about 665 nm for N-aspartyl chlorin e6, and about 650 nm for 5, 10, 15, 20-tetra (m-hydroxyphenyl) chlorin.

As a result of being irradiated, the photosensitizer in its triplet state is thought to interact with oxygen and other compounds to form reactive intermediates, such as singlet oxygen and reactive oxygen species, which can disrupt cellular structures. Possible cellular targets include the cell membrane, mitochondria, lysosomal membranes, and the nucleus. Evidence from tumor and neovascular models indicates that occlusion of the vasculature is a major mechanism of photodynamic therapy, which occurs by damage to the endothelial cells, with subsequent platelet adhesion, degranulation, and thrombus formation.

The fluence during the irradiating treatment can vary widely, depending on the type of photosensitizer used, the type of tissue, the depth of target tissue, and the amount of overlying fluid or blood. Fluences preferably vary from about 10 to about 400 Joules/cm$^2$ and more preferably vary from about 50 to about 200 Joules/cm$^2$. The irradiance varies typically from about 50 mW/cm$^2$ to about 1800 mW/cm$^2$, more preferably from about 100 mW/cm$^2$ to about 900 mW/cm$^2$, and most preferably in the range from about 150 mW/cm$^2$ to about 600 mW/cm$^2$. It is contemplated that for many practical applications, the irradiance will be within the range of about 300 mW/cm$^2$ to about 900 mW/cm$^2$. However, the use of higher irradiances may be selected as effective and having the advantage of shortening treatment times.

The time of light irradiation after administration of the photosensitizer may be important as one way of maximizing the selectivity of the treatment, thus minimizing damage to structures other than the target tissues. The optimum time following photosensitizer administration until light treatment can vary widely depending on the mode of administration, the form of administration such as in the form of liposomes or as a complex with LDL, and the type of target tissue. For example, benzoporphyrin derivative typically becomes present within the target neovasculature within one minute post administration and persists for about fifty minutes, lutetium texaphyrin typically becomes present within the target neovasculature within one minute post administration and persists for about twenty minutes, N-aspartyl chlorin e6 typically becomes present within the target neovasculature within one minute post administration and persists for about twenty minutes, and rose bengal typically becomes present in the target vasculature within one minute post administration and persists for about ten minutes.

Effective vascular closure generally occurs at times in the range of about one minute to about three hours following administration of the photosensitizer. However, as with green porphyrins, it is undesirable to perform the PDT within the first five minutes following administration to prevent undue damage to retinal vessels still containing relatively high concentrations of photosensitizer.

The efficacy of PDT may be monitored using conventional methodologies, for example, via fundus photography or angiography. Closure can usually be observed angiographically by hypofluorescence in the treated areas in the early angiographic frames. During the later angiographic frames, a corona of hyperfluorescence may begin to appear which then fills the treated area, possibly representing leakage from the adjacent choriocapillaris through damaged retinal pigment epithelium in the treated area. Large retinal vessels in the treated area typically perfuse following photodynamic therapy.

Minimal retinal damage is generally found on histopathologic correlation and is dependent on the fluence and the time interval after irradiation that the photosensitizer is administered. It is contemplated that the choice of appropriate photosensitizer, dosage, mode of administration, formulation, timing post administration prior to irradiation, and irradiation parameters may be determined empirically.

It is contemplated that a variety of anti-FasL factors may be combined with other treatments for treating unwanted CNV. The anti-FasL factor can synergistically enhance the activity of the treatment, for example, PDT. In addition, the anti-FasL factor can be used to reduce or delay the recurrence of the condition. The term "anti-FasL factor" is understood to mean any molecule, for example, a protein, peptide, nucleic acid (ribonucleic acid (RNA) or deoxyribonucleic acid (DNA)), peptidyl nucleic acid, organic compound or inorganic compound, that decreases or eliminates the activity of FasL in a mammal. An "effective amount" of an anti-FasL factor is an amount of an anti-FasL factor sufficient to decrease or eliminate the activity of FasL. For example, an effective amount of an anti-FasL antibody is an amount sufficient to reduce or eliminate the binding of FasL to its cognate receptor.

FIG. 1 depicts a representative drawing of the FasL apoptotic pathway. An important mediator of apoptosis is the signaling pathway triggered by the interaction of the receptor Fas with its ligand (FasL). Fas (also known as Apo1/CD95) is a transmembrane death receptor which, upon crosslinking with its natural ligand, FasL, induces apoptosis in Fas receptor-bearing cells. Fas is expressed in a wide variety of tissues, such as the liver, ovary, lung and heart, as well as in myeloid and lymphoblastoid cells. Its cytoplasmic domain contains a 68 amino acid motif that is both necessary and sufficient for the induction of apoptosis (death domain, DD). Upon crosslinking (by the Fas Ligand or polyvalent antibodies), Fas recruits the adaptor FADD (Fas-Associating protein with a Death Domain), also known as MORT1, which, via its N-terminal DED then recruits the pro-enzyme form of caspase-8. The aggregation of Fas, FADD and caspase-8, named the death-inducing signaling complex (DISC), catalyses the proteolytic autoactivation of caspase-8 (induced-proximity model). The resulting subunits p10 and p18 are released into the cytoplasm, where they form an enzymatically active complex that triggers the downstream apoptotic caspase cascade.

In age-related macular degeneration, retinal pigment epithelial cells inhibit choroidal vessel growth through Fas/FasL mediated apoptosis of choroidal endothelial cells. In murine carcinoma, FasL+T lymphocytes suppress tumor vessel growth. Anti-FasL neutralizing antibody has been shown to have anti-angiogenic properties in a murine model of oxygen-induced retinopathy of prematurity. The anti-FasL neutralizing antibody has also been shown to be safe and effective in reducing vascular leakage and endothelial cell damage in a rat model of streptozotocin-induced diabetes. In this model, anti-FasL neutralizing antibody also has a neuroprotective effect by reducing the amount of DNA fragmentation, and therefore apoptosis, in the ganglion cell layer, the outer nuclear and RPE layer, and endothelial cell layer of the retina. The amount of caspase activation is also reduced. Administration of the anti-FasL neutralizing antibody protects against apoptosis in numerous models of inflammatory diseases and toxic insults. Additionally, mice injected with an anti-CD95L antibody 30 minutes after induction of stroke showed a decrease in both infarct volumes and mortality. Thus, the anti-FasL antibody has anti-angiogenic and anti-permeability properties. Moreover, administration of the anti-FasL antibody protects against apoptosis in numerous models of inflammatory diseases and toxic insults.

Studies utilizing an anti-FasL neutralizing antibody, which was administered in a rat model of laser-induced CNV, reduced angiographic leakage and neovascular formation. Furthermore, there is a synergistic effect with PDT in treating CNV, and it reduces significantly the recurrences of CNV. PDT treatment in the rat model of laser-induced CNV induces apoptotic cell death selectively in the endothelial and retinal pigment epithelial cells overlying the treated CNV. This is associated with activation of mitochondria and of executional caspases that ultimately lead to cell demise. Administration of anti-FasL neutralizing antibody in combination with PDT reduces the activation of the mitochondria, reduces the activation of caspases, and, ultimately, decreases the apoptotic death in the endothelial and RPE cell layer. Thus, without being bound to theory, it appears that PDT-related retinal apoptosis occurs through a Fas/FasL mechanism. As a result, the anti-FasL neutralizing antibody can reduce the collateral damage to the retina when given in combination with PDT, for example, by reducing apoptosis of adjacent retinal cells. Furthermore, the combination therapy increases the effectiveness of PDT, reduces the recurrence of CNV, and protects the retina from PDT-induced apoptosis.

Numerous anti-FasL factors are well known and thoroughly documented in the art. Examples of anti-FasL factors useful in the practice of the invention, include, for example, an anti-FasL neutralizing antibody (available, for example, from Pharmingen, San Diego, Calif.); peptides and nucleic acids (for example, anti-FasL aptamers) that bind FasL to prevent or reduce its binding to its cognate receptor; certain antibodies and antigen binding fragments thereof and peptides that bind preferentially to the Fas receptor; antisense nucleotides (and PNAs) and double stranded RNA for RNAi that ultimately reduce or eliminate the production of either FasL or the Fas receptor; soluble Fas; soluble FasL; decoy receptor-3 (DcR3) analogues; matrix metalloproteinases (MMPs); vasoactive intestinal peptide (VIP); pituitary adenylate cyclase-activating polypeptide (PACAP); forskolin; combined use of benazepril and valsartan; nonpeptidic corticotropin-releasing hormone receptor type 1 (CRH-R1)-specific antagonists; mimosine; peptides that produce a defective Fas-FasL complex; platelet-activating factor (PAF); and endothelin-1 (ET-1). These anti-FasL factors can act as direct or indirect antagonists of FasL activity.

The anti-FasL factor may be synthesized using methodologies known and used in the art. For example, proteins and peptides may be synthesized and purified using conventional synthetic peptide chemistries and purification protocols, or expressed as recombinant proteins or peptides in a recombinant expression system (see, for example, "Molecular Cloning" Sambrook et al. eds, Cold Spring Harbor Laboratories). Similarly, antibodies may be prepared and purified using conventional methodologies, for example, as described in "Practical Immunology", Butt, W. R. ed., 1984 Marcel Deckker, New York and "Antibodies, A Laboratory Approach" Harlow et al., eds. (1988), Cold Spring Harbor Press. p Antibodies (e.g., monoclonal or polyclonal antibodies) having sufficiently high binding specificity for the marker or target protein (for example, FasL or its receptor) can be used as anti-FasL factors. As noted above, the term "antibody" is understood to mean an intact antibody (for example, a monoclonal or polyclonal antibody); an antigen binding fragment thereof, for example, an Fv, Fab, Fab' or (Fab)$_2$ fragment; or a biosynthetic antibody binding site, for example, an sFv, as described in U.S. Pat. Nos. 5,091,513; 5,132,405; and 4,704,692. A binding moiety, for example, an antibody, is understood to bind specifically to the target, for example, FasL or its receptor, when the binding moiety has a binding affinity for the target greater than about $10^5$ M$^{-1}$, more preferably greater than about $10^7$ M$^{-1}$.

Antibodies against FasL or its receptor may be generated using standard immunological procedures well known and described in the art. See, for example, Practical Immunology, Butt, N. R., ed., Marcel Dekker, NY, 1984. Briefly, isolated FasL or its receptor is used to raise antibodies in a xenogeneic host, such as a mouse, goat or other suitable mammal. The FasL or its receptor is combined with a suitable adjuvant capable of enhancing antibody production in the host, and injected into the host, for example, by intraperitoneal administration. Any adjuvant suitable for stimulating the host's immune response may be used. A commonly used adjuvant is Freund's complete adjuvant (an emulsion comprising killed and dried microbial cells). Where multiple antigen injections are desired, the subsequent injections may comprise the antigen in combination with an incomplete adjuvant (for example, a cell-free emulsion).

Polyclonal antibodies may be isolated from the antibody-producing host by extracting serum containing antibodies to the protein of interest. Monoclonal antibodies may be produced by isolating host cells that produce the desired antibody, fusing these cells with myeloma cells using standard procedures known in the immunology art, and screening for hybrid cells (hybridomas) that react specifically with the target protein and have the desired binding affinity.

Antibody binding domains also may be produced biosynthetically and the amino acid sequence of the binding domain manipulated to enhance binding affinity with a preferred epitope on the target protein. Specific antibody methodologies are well understood and described in the literature. A more detailed description of their preparation can be found, for example, in Practical Immunology, Butt, W. R., ed., Marcel Dekker, New York, 1984.

To the extent that the anti-FasL factor is a nucleic acid or peptidyl nucleic acid, such compounds may be synthesized by any of the known chemical oligonucleotide and peptidyl nucleic acid synthesis methodologies known in the art (see, for example, PCT/EP92/20702 and PCT/US94/013523) and used in antisense therapy. Anti-sense oligonucleotide and peptidyl nucleic acid sequences, usually 10 to 100 and more preferably 15 to 50 units in length, are capable of hybridizing to a gene and/or mRNA transcript and, therefore, may be used to inhibit transcription and/or translation of a target protein.

Fas or FasL gene expression can be inhibited by using nucleotide sequences complementary to a regulatory region of the Fas or FasL gene (e.g., the Fas or FasL promoter and/or a enhancer) to form triple helical structures that prevent transcription of the Fas or FasL gene in target cells. See generally, Helene (1991) ANTICANCER DRUG DES. 6(6): 569-84, Helene et al. (1992) ANN. NY ACAD. SCI. 660: 27-36; and Maher (1992) BIOESSAYS 14(12): 807-15. The antisense sequences may be modified at a base moiety, sugar moiety or phosphate backbone to improve, e.g., the stability, hybridization, or solubility of the molecule. For example, in the case of nucleotide sequences, phosphodiester linkages may be replaced by thioester linkages making the resulting molecules more resistant to nuclease degradation. Alternatively, the deoxyribose phosphate backbone of the nucleic acid molecules can be modified to generate peptide nucleic acids (see Hyrup et al. (1996) BIOORG. MED. CHEM. 4(1): 5-23). Peptidyl nucleic acids have been shown to hybridize specifically to DNA and RNA under conditions of low ionic strength. Furthermore, it is appreciated that the peptidyl nucleic acid sequences, unlike regular nucleic acid sequences, are not susceptible to nuclease degradation and, therefore, are likely to have greater longevity in vivo. Furthermore, it has been found that peptidyl nucleic acid sequences bind complementary single stranded DNA and RNA strands more strongly than corresponding DNA sequences (PCT/EP92/20702). Similarly, oligoribonucleotide sequences generally are more susceptible to enzymatic attack by ribonucleases than are deoxyribonucleotide sequences, such that oligodeoxyribonucleotides are likely to have greater longevity than oligoribonucleotides for in vivo use.

Additionally, RNAi can serve as an anti-FasL factor. To the extent RNAi is used, double stranded RNA (dsRNA) having one strand identical (or substantially identical) to the target mRNA (e.g. Fas or FasL mRNA) sequence is introduced to a cell. The dsRNA is cleaved into small interfering RNAs (siRNAs) in the cell, and the siRNAs interact with the RNA induced silencing complex to degrade the target mRNA, ultimately destroying production of a desired protein (e.g., Fas or FasL). Alternatively, the siRNA can be introduced directly.

Additionally, aptamers can be used as an anti-FasL factor and may target Fas or FasL. Methods for identifying suitable aptamers, for example, via systemic evolution of ligands by exponential enrichment (SELEX), are known in the art and are described, for example, in Ruckman et al. (1998) J. Biol. Chem. 273: 20556-20567 and Costantino et al. (1998) J. Pharm. Sci. 87: 1412-1420. Furthermore, to the extent that the anti-FasL factor is an organic or inorganic compound, such compounds may be synthesized, extracted and/or purified by standard procedures known in the art.

The type and amount of anti-FasL factor to be administered may depend upon the PDT and cell type to be treated. It is contemplated, however, that optimal anti-FasL factors, modes of administration and dosages may be determined empirically. The anti-FasL factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based FasL factor inhibitors can be administered at doses ranging, for example, from about 0.001 to about 500 mg/kg, more preferably from about 0.01 to about 250 mg/kg, and most preferably from about 0.1 to about 100 mg/kg. With regard to intravitreal administration, the anti-FasL factor, for example, anti-FasL neutralizing antibody, typically is administered periodically as boluses at dosages ranging from about 10 µg to about 5 mg/eye and more preferably from about 100 µg to about 2 mg/eye.

The anti-FasL factor preferably is administered to the mammal prior to PDT, although it may alternatively or additionally be administered during and/or after PDT. Accordingly, it is preferable to administer the anti-FasL factor prior to administration of the photosensitizer. The anti-FasL factor, like the photosensitizer, may be administered in any one of a wide variety of ways, for example, orally, parenterally, or rectally. However, parenteral administration, such as intravenous, intramuscular, subcutaneous, subtenons, transcleral, and intravitreal, is preferred. Administration may be provided as a periodic bolus (for example, intravenously or intravitreally) or as continuous infusion from an internal reservoir (for example, from a bioerodable implant disposed at an intra- or extra-ocular location) or from an external reservoir (for example, from an intravenous bag). The anti-FasL factor may be administered locally, for example, by continuous release from a sustained release drug delivery device immobilized to an inner wall of the eye or via targeted trans-scleral controlled release into the choroid (see, PCT/US00/00207), or the anti-FasL factor may be administered systemically. Additionally, the anti-FasL factor can be administered as an ointment, encapsulated in microspheres or liposomes, or placed in a device for longer release.

The present invention, therefore, includes the use of an anti-FasL factor in the preparation of a medicament for treating, preferably by a PDT-based method, an ocular condition, that preferably is associated with choroidal neovasculature. The anti-FasL factor may be provided in a kit which optionally may comprise a package insert with instructions for how to treat such a condition. A composition comprising both a photosensitizer and an anti-FasL factor may be provided for use in the present invention. The composition may comprise a pharmaceutically acceptable carrier or excipient. Thus, the present invention includes a pharmaceutically acceptable composition comprising a photosensitizer and an anti-FasL factor; as well as the composition for use in medicine. More preferably, however, the invention is for use in combination therapy, whereby an anti-FasL factor and a photosensitizer are administered separately. Preferably, the anti-FasL factor is administered prior to administration of the photosensitizer. Instructions for such administration may be provided with the anti-FasL factor and/or with the photosensitizer. If desired, the anti-FasL factor and photosensitizer may be provided together in a kit, optionally including a package insert with instructions for use. The anti-FasL factor and photosensitizer preferably are provided in separate containers. For each administration, the anti-FasL factor and/or photosensitizer may be provided in unit-dosage or multiple-dosage form. Preferred dosages of photosensitizer and anti-FasL factor, however, are as described above.

In addition, the efficacy and selectivity of the PDT method may be enhanced by combining the PDT with an apoptosis-modulating factor. An apoptosis-modulating factor can be any factor, for example, a protein (for example a growth factor or antibody), peptide, nucleic acid (for example, an antisense oligonucleotide), peptidyl nucleic acid (for example, an anti-sense molecule), organic molecule or inorganic molecule, that induces or represses apoptosis in a particular cell type. For example, it may be advantageous to prime the apoptotic machinery of CNV endothelial cells with an inducer of apoptosis prior to PDT so as to increase their sensitivity to PDT. Endothelial cells primed in this manner are contemplated to be more susceptible to PDT. This approach may also reduce the light dose (fluence) required to achieve CNV closure and thereby decrease the level of damage on surrounding cells such as RPE. Alternatively, the cells outside the CNV may be primed with an a repressor of apoptosis so as to decrease their sensitivity to PDT. In this approach, the PDT at a particular fluence can become more selective for CNV.

Apoptosis involves the activation of a genetically determined cell suicide program that results in a morphologically distinct form of cell death characterized by cell shrinkage, nuclear condensation, DNA fragmentation, membrane reorganization and blebbing (Kerr et al. (1972) Br. J. Cancer 26: 239-257). At the core of this process lies a conserved set of proenzymes, called caspases, and two important members of this family are caspases 3 and 7 (Nicholson et al. (1997) TIBS 22:299-306). Monitoring their activity can be used to assess on-going apoptosis.

It has been suggested that apoptosis is associated with the generation of reactive oxygen species, and that the product of the Bcl-2 gene protects cells against apoptosis by inhibiting the generation or the action of the reactive oxygen species (Hockenbery et al. (1993) Cell 75: 241-251, Kane et al. (1993) Science 262: 1274-1277, Veis et al. (1993) Cell 75: 229-240, Virgili et al. (1998) Free Radicals Biol. Med. 24: 93-101). Bcl-2 belongs to a growing family of apoptosis regulatory gene products, which may either be death antagonists (Bcl-2, Bcl-xL) or death agonists (Bax, Bak.) (Kroemer et al. (1997) Nat. Med. 3: 614-620). Control of cell death appears to be regulated by these interactions and by constitutive activities of the various family members (Hockenbery et al. (1993) Cell 75: 241-251). Several apoptotic pathways may coexist in mammalian cells that are preferentially activated in a stimulus-, stage-, context-specific and cell-type manner (Hakem et al. (1998) Cell 94: 339-352).

The apoptosis-inducing factor preferably is a protein or peptide capable of inducing apoptosis in cells for example, endothelial cells, disposed in the CNV. One apoptosis inducing peptide comprises an amino sequence having, in an N- to C-terminal direction, KLAKLAKKLAKLAK (SEQ ID NO: 2). This peptide reportedly is non-toxic outside cells, but becomes toxic when internalized into targeted cells by disrupting mitochondrial membranes (Ellerby et al. (1999) supra). This sequence may be coupled, either by means of a crosslinking agent or a peptide bond, to a targeting domain, for example, the amino acid sequence known as RGD-4C (Ellerby et al. (1999) supra) that reportedly can direct the apoptosis-inducing peptide to endothelial cells. Other apoptosis-inducing factors include, for example, constatin (Kamphaus et al. (2000) J. Biol. Chem. 14: 1209-1215), tissue necrosis factor α (Lucas et al. (1998) Blood 92: 4730-4741) including bioactive fragments and analogs thereof, cycloheximide (0'Connor et al. (2000) Am. J. Pathol. 156: 393-398), tunicamycin (Martinez et al. (2000) Adv. Exp. Med. Biol. 476: 197-208), and adenosine (Harrington et al. (2000) Am. J. Physiol. Lung Cell Mol. Physiol. 279: 733-742). Furthermore, other apoptosis-inducing factors may include, for example, anti-sense nucleic acid or peptidyl nucleic acid sequences that reduce or turn off the expression of one or more of the death antagonists, for example (Bcl-2, Bcl-xL). Antisense nucleotides directed against Bcl-2 have been shown to reduce the expression of Bcl-2 protein in certain lines together with increased phototoxicity and susceptibility to apoptosis during PDT (Zhang et al. (1999) Photochem. Photobiol. 69: 582-586). Furthermore, an 18mer phosphorothiate oligonucleotide complementary to the first six codons of the Bcl-2 open reading frame, and known as G3139, is being tested in humans as a treatment for non-Hodgkins' lymphoma.

Apoptosis-repressing factors include, survivin, including bioactive fragments and analogs thereof (Papapetropoulos et al. (2000) J. Biol. Chem. 275: 9102-9105), CD39 (Goepfert et al. (2000) Mol. Med. 6: 591-603), BDNF (Caffe et al. (2001) Invest. Ophthalmol. Vis. Sci. 42: 275-82), FGF2 (Bryckaert et al. (1999) Oncogene 18: 7584-7593), Caspase inhibitors (Ekert et al. (1999) Cell Death Differ 6: 1081-1068) and pigment epithelium-derived growth factor including bioactive fragments and analogs thereof. Furthermore, other apoptosis-repressing factors may include, for example, anti-sense nucleic acid or peptidyl nucleic acid sequences that reduce or turn off the expression of one or more of the death agonists, for example (Bax, Bak).

To the extent that the apoptosis-modulating factor is a protein or peptide, nucleic acid, peptidyl nucleic acid, or organic or inorganic compound, it may be synthesized and purified by one or more the methodologies described relating to the synthesis of the anti-FasL factor.

The type and amount of apoptosis-modulating factor to be administered may depend upon the PDT and cell type to be treated. It is contemplated, however, that optimal apoptosis-modulating factors, modes of administration and dosages may be determined empirically. The apoptosis modulating factor may be administered in a pharmaceutically acceptable carrier or vehicle so that administration does not otherwise adversely affect the recipient's electrolyte and/or volume balance. The carrier may comprise, for example, physiologic saline.

Protein, peptide or nucleic acid based apoptosis modulators can be administered at doses ranging, for example, from about 0.001 to about 500 mg/kg, more preferably from about 0.01 to about 250 mg/kg, and most preferably from about 0.1 to about 100 mg/kg. For example, nucleic acid-based apoptosis inducers, for example, G318, may be administered at doses ranging from about 1 to about 20 mg/kg daily. Furthermore, antibodies may be administered intravenously at doses ranging from about 0.1 to about 5 mg/kg once every two to four weeks. With regard to intravitreal administration, the apoptosis modulators, for example, antibodies, may be administered periodically as bolus dosages ranging from about 10 µg to about 5 mg/eye and more preferably from about 100 µg to about 2 mg/eye.

The apoptosis-modulating factor preferably is administered to the mammal prior to PDT. Accordingly, it is preferable to administer the apoptosis-modulating factor prior to administration of the photosensitizer. The apoptosis-modulating factor, like the photosensitizer and anti-FasL factor, may be administered in any one of a wide variety of ways, for example, orally, parenterally, or rectally. However, parenteral administration, such as intravenous, intramuscular, subcutaneous, and intravitreal is preferred. Administration may be provided as a periodic bolus (for example, intravenously or intravitreally) or by continuous infusion from an internal reservoir (for example, bioerodable implant disposed at an intra- or extra-ocular location) or an external reservoir (for example, and intravenous bag). The apoptosis modulating factor may be administered locally, for example, by continuous release from a sustained release drug delivery device immobilized to an inner wall of the eye or via targeted transscleral controlled release into the choroid (see, PCT/US00/00207).

The foregoing methods and compositions of the invention are useful in treating unwanted choroidal neovasculature and thereby ameliorate the symptoms of ocular disorders including, for example, AMD, ocular histoplasmosis syndrome, pathologic myopia, angioid streaks, idiopathic disorders, choroiditis, choroidal rupture, overlying choroid nevi, and inflammatory diseases, and it is contemplated that the same methods and compositions may also be useful in treating other forms of ocular neovasculature. More specifically, the methods and compositions of the invention may likewise be useful at treating and removing or reducing corneal neovasculature, iris neovasculature, retinal neovasculature, retinal angiomas and choroidal hemangiomas.

The invention is illustrated further by reference to the following non-limiting example.

EXAMPLE 1

Anti-FasL Factor Enhances PDT

PDT is an effective treatment for CNV but may require multiple treatments to limit vision loss. Preclinical studies have demonstrated damage to adjacent retinal structures which may accumulate with multiple treatments. The neuroprotective properties of an anti-FasL neutralizing antibody may offer neuroprotection and improve the effectiveness of PDT. To investigate the efficacy of PDT in combination with an anti-FasL neutralizing antibody in a laser injury model of CNV in the rat, the following experiment was undertaken.

Methods

Induction of Choroidal Neovascularization

Choroidal neovascular membranes were induced in Brown-Norway rats using an Argon/dye laser. Briefly, Brown-Norway rats (Charles River Laboratory, Wilmington, Mass.) were anesthetized via an intramuscular injection of 50 mg/kg of ketamine hydrochloride and 10 mg/kg of xylazine. Pupils were dilated with a topical application of 5% phenylephrine and 0.8% tropicamide. Six laser spots were induced in each eye using an Argon/dye laser (532 Argon/dye laser, Coherent medical laser, Santa Clara, Calif.) by a single investigator.

Administration of Anti-FasL Antibody in vivo

These rats were continuously administered (via subcutaneous pump) either anti-FasL neutralizing antibody or isotype-matched control at a total dose of about 5 mg/kg. Briefly, to achieve steady drug levels in the circulation of animals, the anti-FasL antibody (anti-rat antibody MFL4, Armenian hamster IgG, Pharmingen, San Diego, Calif.) or the isotype-matched control antibody (Armenian hamster anti-TNP IgG, Pharmingen, San Diego, Calif.) was administered by slow intraperitoneal release from osmotic pumps (Alzet, Cupertino, Calif.) instead of repeated intraperitoneal injections. Immediately following the induction of choroidal neovascularization, osmotic pumps (Alzet, Cupertino, Calif.) were implanted. Two hundred microliters of each antibody at a concentration of 5 mg/ml were inserted in each osmotic pump, which released 0.5 µl/hr for 14 days.

Fluoresce in Angiography

Fluorescein angiography was performed 14 days after the initial laser treatment using a digital fundus camera system (Model TRC 501 A, Topcon, Paramus, N.J.) and standard fluorescein filters to determine if CNV induction was successful. CNV closure on fluorescein angiograms was assessed 24 hours and seven days after verterporfin PDT in a masked fashion using grading standards. Each animal was given a bolus injection of 1 ml of 1% sodium fluorescein (Akorn Inc, Decatur, Ill.) in saline intraperitoneally, and the timer was started as soon as the fluorescein bolus was injected. All angiograms were evaluated in masked fashion by two independent retina specialists using grading standards and severity of CNV (baseline FAs) and CNV closure (24 hour FAs).

Photodynamic Therapy in Rats

PDT with verteporfin was performed 14 days after CNV induction. Briefly, rats were anesthetized, and verteporfin, at a dose of 3 mg/m$^2$, was injected into the tail veins of rats immobilized in a stereotactic frame. The body surface area of each rat was determined based on their weight according to a nomogram developed by Gilpin. One eye of each animal was selected, avoiding eyes that had large subretinal hemorrhages that the PDT spot could not cover. Fifteen minutes after the injection, laser light at 689 nm was administered through the pupil with a diode laser (Coherent medical laser, Santa Clara, Calif.) delivered through a slit lamp adaptor (Laserlink, Coherent medical laser, Santa Clara, Calif.). The laser spot size was set at 759 μm on the plane of the retina. The laser had a constant irradiance of 600 mW/cm$^2$ and a fluence of 25 J/cm$^2$ which was delivered for 17 or 42 seconds to achieve total energy doses of 10 J/cm$^2$.

Western Blotting

The levels of protein expression of caspase 3 and caspase 8, Bax, Bid, Bcl-2, and cytochrome c (Pharmacia) were evaluated by Western blotting. Briefly, whole retinae were lysed for 30 minutes on ice in lysis buffer (50 mM Tris-HCl, pH 8, with 120 mM NaCl and 1% NP-40) supplemented with the Complete-mini mixture of proteinase inhibitors. The samples were cleared by micro-centrifugation (14,000 rpm, 30 minutes, 4° C.) and assessed for protein concentration. Thirty micrograms of protein/sample were electrophoresed in a 12% sodium dodecyl sulphate (SDS)-polyacrylamide gel (SDS-PAGE) and electroblotted onto nitrocellulose membranes. After a one hour incubation in blocking solution (20% IgG-free normal horse serum in phosphate-buffered saline (PBS)), the membranes were exposed overnight at 4° C. to the respective primary antibody. Following washing in PBS, the respective secondary peroxidase-labeled antibody was applied at a 1:10,000 dilution for one hour at room temperature. The proteins were visualized with the enhanced chemiluminescence technique (Amersham Pharmacia Biotech, Piscataway, N.J.).

Enzyme Activity Assays for Caspase 3 and 8

The enzymatic activity of caspases 3 and 8 were detected in retinal lysates with the Apo Alert kit (Clontech, Palo Alto, Calif.).

Tunel Staining

Apoptotic cells were analyzed using the TUNEL technique. Briefly, free 3'OH DNA termini were labeled using the TUNEL procedure according to the manufacturer's recommendations (Intergen, N.Y.). TUNEL was performed with horseradish peroxidase detection in sections from formalin-fixed, paraffin embedded retinas. Whole eyes from rats with or without laser-induced CNV treated with the anti-FasL antibody or the isotype-matched control antibody were fixed in 4% paraformaldehyde overnight at 4° C. Then, TUNEL staining was performed.

Statistics

Differences in CNV induction between treatment groups were evaluated using chi-square tests. Lesions that did not show significant leakage were excluded from the statistical analysis. Retinal levels of Bcl-2, Bax, Bcl-xL, and Bid were measured by Western blotting, and cystolic and mitochondrial levels of cytochrome c were measured by a modified ELISA method. Activation of caspases-3 and -6 were measured with a modified ELISA method in whole retinal lysates.

Results

Anti-FasL Antibody Treatment Reduces Angiographic Leakage in Laser-induced CNV

To assess whether the anti-FasL antibody treatment influences the angiographic leakage in the laser-induced CNV model, the percentage of lesions that were closed in rats that received the anti-FasL antibody treatment was compared to the percentage from those that received the control antibody treatment. The percentage of angiographically "leaky" lesions (grade IIA+IIB) among the anti-FasL antibody treated rats was 82% and was 97.4% in the control antibody treated rats (P<0.000 1). Whereas, the percentage of the angiographically non-leaky and less leaky lesions (grade I+0) was 19% in rats that received the anti-FasL antibody treatment and 2.6% in the control antibody treated rats (FIG. 6). Thus, FIG. 6 provides evidence that anti-FasL antibody treatment reduces angiographic leakage in laser-induced CNV.

Anti-FasL Antibody Treatment Reduces PDT-induced Angiographic Leakage in Laser-induced CNV To assess whether the anti-FasL treatment influences the angiographic leakage after PDT in the laser induced CNV model, the percentage of lesions that were closed in rats that received PDT and the anti-FasL antibody treatment was compared to the percentage from those that received the control treatment. Because the anti-FasL antibody treatment reduced the angiographic leakage in a statistically significant manner relative to the control antibody, lesions on which to perform PDT were selected that had an equal degree of angiographic leakage in the two antibody-treated populations. The percentage of closed lesions among the anti-FasL antibody and PDT treated rats was 100% and was 69% in the control and PDT treated rats (FIG. 5). Thus, FIG. 5 provides evidence that anti-FasL antibody treatment reduces angiographic leakage after PDT. Because the anti-FasL antibody had a marginal effect on non-leaky lesions as shown by the comparison between laser-induced CNV animals receiving anti-FasL antibody treatment and control antibody treatment (19% vs. 2.6%, FIG. 6), the fact that 100% of the animals receiving combined anti-FasL antibody and PDT treatment showed closed lesions in comparison to 69% of the animals receiving combined control antibody and PDT treatment indicates that the combination produces more than an additive effect and is synergistic.

PDT Increases the Expression of the Fas Receptor in the Rat Retina

Figure 3:
FIG. 3 provides evidence that PDT increases the expression of the Fas receptor in the rat retina.

It is understood that treatment with the photosensitizer verteporfin increases the apoptotic cell death both in vivo and in vitro. It was suggested that PDT acts in concert with the Fas apoptotic signaling pathway, because a Fas-activating antibody can potentiate the PDT-induced cell death of thymic cells in vivo. This experiment indicated that verteporfin PDT increases the retinal levels of the apoptotic death receptor, Fas, an indication that the Fas/FasL pathway plays a causative role in the apoptotic retinal cell death after PDT (FIG. 3). Thus, FIG. 3 provides evidence that PDT increases the expression of the Fas receptor in the rat retina.

Anti-FasL Antibody Treatment Reduces PDT-induced Apoptosis in Laser-induced CNV

To investigate the role of Fas/FasL in verteporfin-PDT, the occurrence of apoptotic cell death in the retinas of rats that had received, concurrent with PDT, the anti-FasL antibody treatment or the control antibody was studied. It was found that rats that had received the control antibody treatment plus PDT showed apoptotic cells in the RPE, photoreceptor and endothelial cell layer, whereas the anti-FasL antibody treatment significantly reduced this apoptotic death from PDT. Rats that received only the anti-FasL antibody or control antibody showed a minimal amount of apoptotic death.

Figure 4:
FIG. 4 provides evidence that anti-FasL treatment prevents activation of caspase 3 after PDT.
Figure 7:
FIG. 7 provides evidence that anti-FasL treatment reduces PDT-induced caspase 8 activation in laser-induced CNV.

Anti-FasL Antibody Treatment Prevents PDT-induced Activation of Caspases 3 and 8 in Laser-induced CNV Fas/FasL mediated apoptotic cell death involves the activation of apical (receptor mediated) and executional caspases. Rats treated with PDT and control antibody showed cleavage of the proform of caspases 3 and 8 to their respective activated fragments. The immunoblotting results were confirmed with caspase activity assays. The anti-FasL antibody inhibited the PDT-induced activation of caspases (FIGS. 4 and 7). Thus, FIG. 4 provides evidence that anti-FasL antibody treatment prevents activation of caspase 3 after PDT, and FIG. 7 provides evidence that anti-FasL antibody treatment reduces PDT-induced caspase 8 activation in laser-induced CNV.

Figure 9:
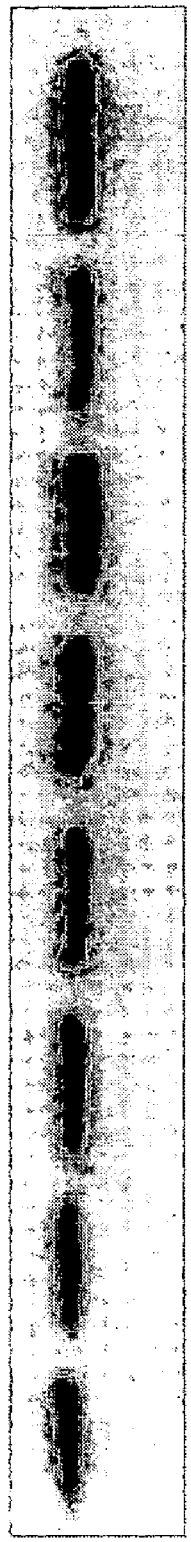
FIG. 9 provides evidence that anti-FasL treatment reduces PDT-induced Bax upregulation in laser-induced CNV.
Figure 10:
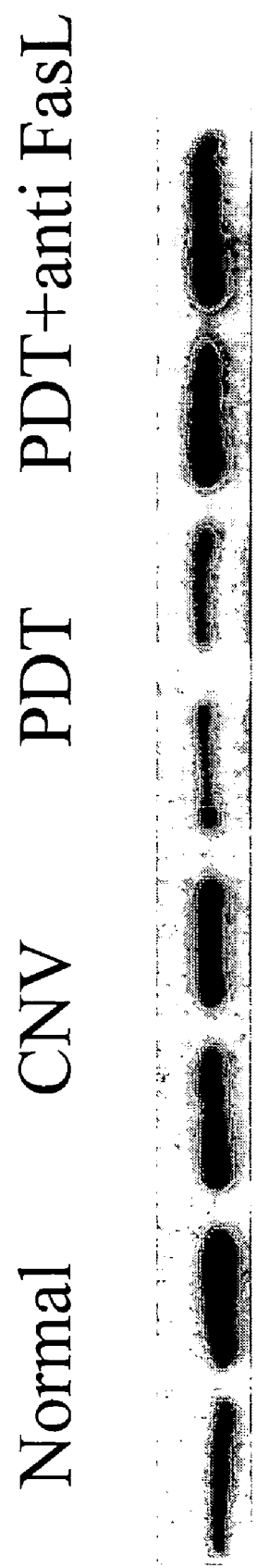
FIG. 10 provides evidence that anti-FasL treatment reduces PDT-induced Bcl-2 downregulation in laser-induced CNV.

Anti-FasL Antibody Treatment Reduces PDT-induced Bax Upregulation and Bcl-2 Downregulation in Laser-induced CNV Apoptosis and cell survival is the outcome of a delicate balance between anti-apoptotic genes, such as Bcl-2, and pro-apoptotic genes, such as Bax, which were shown to influence Fas-mediated apoptosis in a variety of models. In the present animal model, PDT-induced apoptosis is associated with downregulation of Bcl-2 protein levels and upregulation of Bax protein levels. Treatment with the anti-FasL antibody, but not the control antibody, attenuates the PDT-induced downregulation of Bcl-2 level and upregulation of Bax level (FIGS. 9 and 10). Thus, FIG. 9 provides evidence that anti-FasL antibody treatment reduces PDT-induced Bax upregulation in laser-induced CNV, and FIG. 10 provides evidence that anti-FasL antibody treatment reduces PDT-induced Bcl-2 downregulation in laser-induced CNV.

Figure 2:
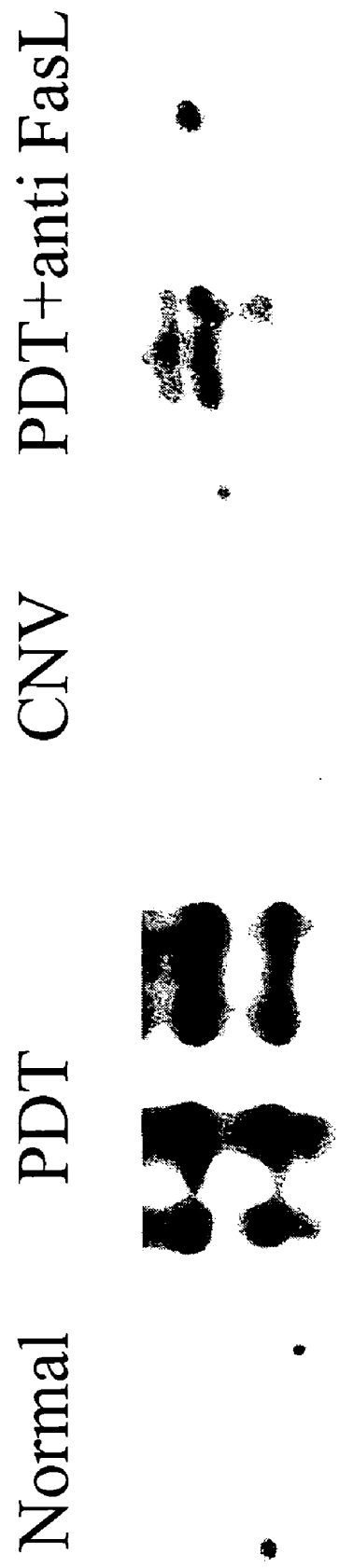
FIG. 2 provides evidence that anti-FasL treatment prevents cleavage of bid after PDT.

Anti-FasL Antibody Treatment Prevents PDT-induced Cleavage of Bid in Laser-induced CNV In the present animal model, PDT-induced apoptosis is associated with cleavage of Bid. Treatment with the anti-FasL antibody, but not the control antibody, attenuates the PDT-induced cleavage of Bid (FIG. 2). Thus, FIG. 2 provides evidence that anti-FasL antibody treatment prevents cleavage of Bid after PDT.

Figure 8:
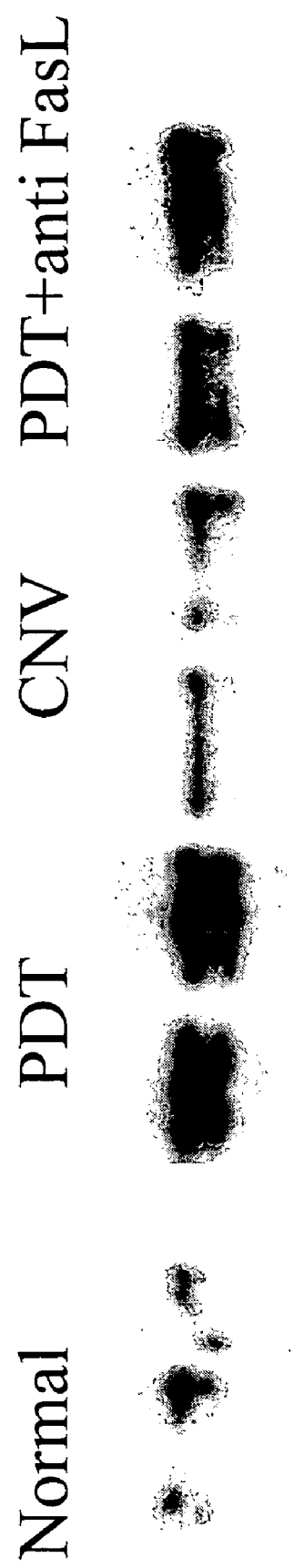
FIG. 8 provides evidence that anti-FasL treatment reduces PDT-induced cytochrome c release in laser-induced CNV.

Anti-FasL Antibody Treatment Reduces PDT-induced Cytochrome c Release in Laser-induced CNV In the present animal model, PDT-induced apoptosis is associated with release of mitochondrial cytochrome c into the cytoplasm. Treatment with the anti-FasL antibody, but not the control antibody, attenuates the PDT-induced release of mitochondrial cytochrome c into the cytoplasm (FIG. 8). Thus, FIG. 8 provides evidence that anti-FasL antibody treatment reduces PDT-induced cytochrome c release in laser-induced CNV.

Discussion

In the present study, the efficacy of PDT in combination with a FasL neutralizing antibody was investigated. It was found that continuous subcutaneous administration of the anti-FasL antibody, but not the isotype matched control antibody, reduced the angiographic leakage from CNV and increased the efficacy of verteporfin PDT on CNV closure.

These findings suggest that apoptotic mechanisms may participate in retinal cell loss during PDT. The involvement of the Fas/FasL receptor/ligand pair and the Bcl-2 family members were also investigated in this model. The Bcl-2 family includes several anti-apoptotic members, such as Bcl-2 and Bcl-xL, whereas Bax and the cleaved form of Bid promote apoptosis. The balance between pro-and anti-apoptotic members of the Bcl-2 family regulates the fate of mitochondrial cytochrome c. When the pro-apoptotic stimuli predominate, cytochrome c moves from the mitochondria to the cytoplasm, where, together with Apaf1, it activates pro-caspase-9. The active form of caspase-9 then activates the executioner caspases-3 and -6. PDT decreased the retinal levels of Bcl-2 and Bcl-xL, increased the levels of Bax, and induced Bid cleavage. The release of cytochrome c to the cytosol and activation of caspases -3 and -6 also were detected.

Treatment with the anti-FasL neutralizing antibody, but not the isotype matched control antibody, reversed the above-mentioned changes. This suggests a role for the Fas/FasL pathway in triggering this apoptotic cascade. The Fas receptor can activate caspase-9 and, subsequently, caspases-3 and -6, via two pathways. The first pathway is activation of caspase-8, which can directly cleave and activate caspase-9 (type I pathway). The second pathway is, when the level of caspase-8 activation is insufficient to cleave caspase-9 due to low endogenous pro-caspase-8 expression or due to the presence of caspase-8 inhibitors such as FLIP, amplification of the apoptotic signal of caspase-8 via the mitochondria (type II pathway). Specifically, caspase-8 cleaves Bid into its active, pro-apoptotic form. This then triggers cytochrome c release from the mitochondria and the above-mentioned activation of caspase-9 and the downstream executioner caspases (See FIG. 1). The ability of a Fas/FasL neutralizing agent to inhibit the downstream apoptotic signaling pathway in this study confirms its role in triggering retinal cell apoptosis in PDT.

The ability of a Fas/FasL inhibitor to suppress retinal cell apoptosis in PDT-treated retinae may also have therapeutic implications. Concurrent treatment with a Fas/FasL neutralizing agent, such as an anti-Fas or anti-FasL antibody, or possibly with a caspase inhibitor, may limit the damage to adjacent normal structures that occurs during PDT. This may allow more intensive PDT treatments, thus potentially improving PDT results. Due to the involvement of the Fas apoptotic pathway in several other disease models, such as hepatitis, there is strong interest in drug development of Fas/FasL inhibitors that would be effective and safe for human use.

In conclusion, continuous subcutaneous administration of the anti-FasL neutralizing antibody, and not the isotype matched control antibody, reduced the angiographic leakage from CNV (97.4% of the lesions in the animals treated with the control antibody were stage IIA and IIB versus 82% in the anti-FasL antibody treated group, $P<0.001$) and increased the efficacy of verteporfin PDT on CNV closure (69% of the lesions in the animals treated with the control antibody and PDT were angiographically not perfused versus 100% of lesions treated with anti-FasL antibody and PDT). PDT decreased the retinal levels of Bcl-2 and Bcl-xL, increased the levels of Bax, and induced cleavage of Bid and release of cytochrome c into the cytosol. PDT also induced activation of caspases-3 and -6 in the retina. Treatment with the anti-FasL neutralizing antibody, but not the isotype-matched control, reversed these changes.

Anti-FasL antibody administration decreased the agiographic leakage, increased the efficacy of Verteporfin PDT for CNV closure in a rat model, and reduced the collateral apoptotic damage induced by PDT. This suggests that the combination of PDT with anti-FasL neutralizing agents (i.e., anti-FasL factors) may limit damage to normal structures and improve PDT results.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

The entire disclosure of each of the patent documents and scientific publications disclosed hereinabove is expressly incorporated herein by reference for all purposes.

What is claimed is:

1. A method of treating unwanted choroidal neovasculature by reducing leakage therefrom in a mammal, the choroidal neovasculature comprising endothelial cells, the method comprising the steps of:
   (a) administering to the mammal an anti-FasL factor in an amount sufficient to permit an effective amount to localize in the choroidal neovasculature, wherein the anti-FasL factor is selected from the group consisting of an anti-FasL antibody, an anti-Fas antibody, decoy receptor 3, and a decoy receptor-3 analog, and reduces apoptotic photoreceptor cell death and decreases the activity of FasL in a mammal by direct action on FasL or its receptor;
   (b) administering to the mammal an amount of photosensitizer sufficient to permit an effective amount to localize in the choroidal neovasculature; and
   (c) irradiating the choroidal neovasculature with laser light such that the light is absorbed by the photosensitizer so as to reduce leakage from the choroidal neovasculature, wherein the combination of steps (a), (b), and (c) is synergistically effective in reducing leakage.

2. The method of claim 1, wherein the mammal is a primate.

3. The method of claim 2, wherein the primate is a human.

4. The method of claim 1, wherein the anti-FasL factor is administered to the mammal prior to administration of the photosensitizer.

5. The method of claim 1, wherein the photosensitizer is an amino acid derivative, an azo dye, a xanthene derivative, a chlorin, a tetrapyrrole derivative, or a phthalocyanine.

6. The method of claim 5, wherein the photosensitizer is lutetium texaphyrin, a benzoporphyrin, a benzoporphyrin derivative, a hematoporphyrin, or a hematoporphyrin derivative.

7. The method of claim 1, wherein the anti-FasL factor comprises is an anti-FasL antibody.

8. The method of claim 1, wherein the anti-FasL factor reduces binding of FasL to its receptor.

9. The method of claim 1, wherein the anti-FasL factor reduces FasL signaling.

10. The method of claim 1, wherein the anti-FasL factor is an anti-Fas antibody.

11. The method of claim 1, wherein the anti-FasL factor is decoy receptor-3.

12. The method of claim 1, wherein the anti-FasL factor is a decoy receptor-3 analog.

13. The method of claim 6, wherein the photosensitizer is lutetium texaphyrin.

14. The method of claim 6, wherein the photosensitizer is a benzoporphyrin.

15. The method of claim 6, wherein the photosensitizer is a benzoporphyrin derivative.

* * * * *

UNITED STATES PATENT AND TRADEMARK OFFICE
CERTIFICATE OF CORRECTION

| | | |
|---|---|---|
| PATENT NO. | : 7,803,375 B2 | |
| APPLICATION NO. | : 11/359887 | |
| DATED | : September 28, 2010 | |
| INVENTOR(S) | : Evangelos S. Gragoudas et al. | |

It is certified that error appears in the above-identified patent and that said Letters Patent is hereby corrected as shown below:

In Claim 7, column 22, line 37, delete "comprises."

Signed and Sealed this
Eleventh Day of January, 2011

David J. Kappos
*Director of the United States Patent and Trademark Office*

SEQUENCE LISTING

```
<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Synthetic sequence

<400> SEQUENCE: 1

Ala Cys Asp Cys Arg Gly Asp Cys Phe Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic sequence

<400> SEQUENCE: 2

Lys Leu Ala Lys Leu Ala Lys Lys Leu Ala Lys Leu Ala Lys
1               5                   10
```